United States Patent [19]

Schaafsma et al.

[11] 3,950,438

[45] Apr. 13, 1976

[54] PREPARATION OF RESORCINOL AND ALKYL-SUBSTITUTED DERIVATIVES THEREOF

[75] Inventors: Sijbrandus E. Schaafsma, Beek; Johannes E. L. Claassens, Heerlen; Egidius J. M. Verheijen, Sittard, all of Netherlands

[73] Assignee: Stamicarbon B.V., Geleen, Netherlands

[22] Filed: Mar. 11, 1974

[21] Appl. No.: 450,219

[30] Foreign Application Priority Data

Mar. 14, 1973 Italy .................................. 03537/70

[52] U.S. Cl. ...... 260/621 R; 260/586 C; 260/617 R; 260/618 R; 260/618 F; 260/638 R
[51] Int. Cl.² .................... C07C 37/00; C07C 45/00; C07C 27/00
[58] Field of Search ........ 260/621 R, 621 H, 586 R, 260/617 R, 618 R, 625, 586 C

[56] References Cited
UNITED STATES PATENTS
3,580,970 5/1971 Swift .............................. 260/621 H
3,691,102 9/1972 Swift .............................. 260/621 H OTHER PUBLICATIONS
Vorlander, *Liebigs Annalen*, 294:270–271.
Kost et al., *Zhurnal Obshch. Khim.*, Vol. 32, pp. 3983–3986, (1962) cited in *C.A.* Vol. 58, p. 13808d.
Bornstein et al., *Chem. Ab.*, Vol. 48, p. 9933d, (1954).

*Primary Examiner*—Norman Morgenstern
*Attorney, Agent, or Firm*—Cushman, Darby & Cushman

[57] ABSTRACT
Process for the preparation of resorcinols of the general formula:

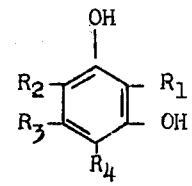

wherein $R_1$, $R_2$, $R_3$, and $R_4$, which are the same or different, are each hydrogen or an alkyl group containing up to 6 carbon atoms, and the total number of carbon atoms of $R_1$, $R_2$, $R_3$, and $R_4$ is no more than 12 carbon atoms, which comprises contacting keto esters of the general formula

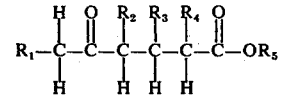

wherein $R_1$, $R_2$, $R_3$, and $R_4$ are as defined above, and $R_5$ is an alkyl, cycloalkyl, or monocyclic or bicyclic aryl or arylalkyl group containing up to 12 carbon atoms, with a dehydrogenation catalyst at a temperature of about 100°C to 500°C.

11 Claims, No Drawings

PREPARATION OF RESORCINOL AND ALKYL-SUBSTITUTED DERIVATIVES THEREOF

The present invention relates to a process for preparing resorcinol and alkyl-substituted derivatives of resorcinol.

It is known (see *Journal of General Chemistry U.S.S.R.*, volume 32, 1962, pages 3908–3911) that various delta-keto-esters, when treated with sodium methanolate (sodium methoxide) followed by neutralization of the resulting alkaline mixture with sulphuric acid, can be cyclized into a substituted or unsubstituted dihydroresorcinol (cyclohexane-1,3-dione), with formation of an alcohol corresponding to the alcohol moiety of the ester group. The dehydrogenation of dihydroresorcinol to resorcinol with the aid of a dehydrogenation catalyst has also been described (see British Pat. Specification No. 1,188,387 and U.S. Pat. No. 3,627,833). Starting from a delta-keto-ester it is possible, therefore, to prepare resorcinol in a known way, by first carrying out cyclization and by subsequently dehydrogenating the dihydroresorcinol that is obtained. A major disadvantage of such a two-stage process, however, is that the cyclization calls for a rather large amount of sodium methanolate and sulphuric acid, and the sodium sulphate that is obtained as a by-product is only of little value. Another disadvantage is that the yield achieved in case of dehydrogenation of the dihydroresorcinol is rather low (see British Pat. Specification No. 1,188,387).

A process has now been found which obviates these disadvantages and permits delta-keto-esters to be converted in one step into the corresponding resorcinol. The process according to the present invention is characterized in that a keto-ester of the general formula:

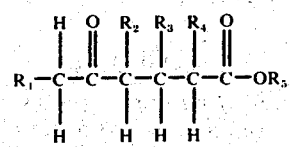

is contacted at an elevated temperature with a dehydrogenation catalyst, and that from the resulting reaction mixture a resorcinol is recovered of the general formula:

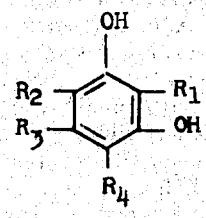

In the above formulas the substituents $R_1$, $R_2$, $R_3$ and $R_4$, which are the same or different, each represent hydrogen or an alkyl group containing up to 6 carbon atoms, provided that the total number of carbon atoms of these substituents $R_1$–$R_4$ does not amount to more than 12, and $R_5$ represents a hydrocarbon group containing up to 12 atoms such as an alkyl, cycloalkyl, monocyclic or bicyclic aryl, or arylalkyl group.

In the present process an alcohol is also formed of the general formula $R_5OH$, wherein $R_5$ is as defined above. This alcohol by-product may be recovered by fractional distillation of the reaction mixture obtained and be applied for preparation of the keto-ester starting material, for instance either according to the method mentioned in the periodical article referred to above or by forming an ester of an alpha-beta-unsaturated carboxylic acid and by converting this ester to a ketone according to the method described in the U.S. Pat. application Ser. No. 413,436, filed Nov. 2, 1973.

For the hydrocarbon group $R_5$ of the keto-ester starting material, various groups are suitable, in particular alkyl-, cycloalkyl-, arylalkyl-, and aryl-groups. Of the arylalkyl groups, monocyclic and bicyclic arylalkyl groups are especially preferred, e.g., benzyl. Likewise, monocyclic and bicyclic aryl groups, e.g. phenyl and naphthyl are preferred. Preferably, $R_5$ is an alkyl group containing up to 6 carbon atoms. Especially preferred are methyl, ethyl, n-propyl, isopropyl, n-butyl, sec-butyl, n-pentyl and n-hexyl groups. Similar groups are preferred when $R_1$–$R_4$ are alkyl.

The process according to the invention may be carried out in both the gas phase and the liquid phase at various temperatures, in particular temperatures of about 100°–500°C. Conducting the process in the gas phase has the advantage in that the catalyst and the reaction mixture can be separated in a simple manner. In carrying out the process in the gas phase, the temperature chosen preferably lies between 200° and 400°C because at a sufficient conversion of the keto-ester a reasonable efficiency can then be reached. Which temperature within this range is the most suitable is determined, among other things, by the catalyst used. The optimum temperature will be readily determined by routine experimentation.

A wide variety of dehydrogenation catalysts may be used in the present process of the invention. Typical dehydrogenation catalysts are disclosed in *Modern Synthetic Reactions*, H.O. House, 2nd ed., 1972, Chapter I. Especially preferred are catalysts containing a metal or a compound of a metal selected from the group consisting of iron, cobalt, nickel, ruthenium, rhodium, palladium, osmium, iridium, platinum and copper. Particularly suitable are the metals palladium, platinum and nickel. The catalysts are usually applied on a carrier, such as carbon, silicon dioxide, aluminum oxide, magnesium oxide and mixtures thereof. Preference is given to application of palladium and/or platinum on carbon catalysts because a very satisfactory efficiency can then be achieved. With application of other catalysts, such as nickel on silicon dioxide or aluminum oxide, by-products can be formed, like phenol and cyclohexane-1,3-dione when a 4-oxopentane-carboxylic acid ester is used, and, therefore, the suitability of a particular catalyst is also determined by the value of the by-products obtained.

The process according to the invention may be carried out in various ways. Particularly suitable for large-scale processes is a mode according to which the starting compound is diluted in the gaseous state with an inert gas, like nitrogen and carbon dioxide, and is contacted with the catalyst which is in the form of a fixed bed or a so-called fluid bed. It has been found that if, at the same time, hydrogen is then added to the gaseous starting mixture, for instance 1–15 moles per mole of keto-ester, the activity of the catalyst will remain at a high level for a longer period of time. In the above embodiment the space velocity may be varied, for instance between 0.1 and 2 grams of keto-ester per milliliter of catalyst per hour.

Upon cooling of the gaseous reaction mixture that is obtained, a condensate is obtained from which, by fractional distillation, the desired product and, possibly, non-converted starting product, can be recovered. Recovery of the desired product from this condensate can also be realized by extraction with, for instance, water. Any by-products formed can also be recovered in this distillation or extraction.

Although the gas phase process above is preferred particularly in large-scale operations, the reaction can also be conducted in an inert solvent. Typical solvents are mentioned in the text referred to above. Typical solvents are the inert organic solvents, boiling above 100°C, such as toluene, the xylenes, diphenyl ether and chloro-substituted aromatics, e.g. monochlorobenzene.

The resorcinols obtained according to the invention may be used for various purposes, for instance for preparing glues and dyes and in the preparation of resorcinol-formaldehyde resins.

The invention will be illustrated in more detail in the following examples, which should not be construed as limiting the scope of the invention in any way.

EXAMPLE I

A gaseous mixture of nitrogen, hydrogen and methyl 5-oxo-hexanoate was made to descend, for four hours, through a vertical, tubular reactor 18 mm. in diameter and 400 mm in length, containing 30 ml of catalyst (10.1% by weight of nickel on alpha-aluminum oxide as carrier; bulk density 0.72 g per ml) in the form of spherules having a diameter of about 4 mm. The temperature of the catalyst in the reactor was kept at 338°–340°C by means of a heating jacket. Prior to the experiment being conducted, the catalyst had been activated by passing hydrogen through the reactor for 24 hours at 500°C. The gaseous mixture (4.0 moles of hydrogen and 2.2 moles of nitrogen per mole of the methyl 5-oxo-hexanoate) had been obtained by evaporation of the liquid methyl ester and admixture of the resultant vapor with hydrogen and nitrogen. The space velocity amounted to 0.2 g of methyl ester per mm of catalyst per hour.

After an operating period of two hours, the resulting gas mixture was passed for two hours through a collecting vessel which had been cooled to −20°C, whereupon the condensed reaction product was heated to room temperature. According to a gas-chromatographic analysis the product (11.3 g) contained 79.5% by weight of methyl 5-oxo-hexanoate, 6.5% by weight of resorcinol, 4.2% by weight of dihydroresorcinol, 1.1% by weight of phenol, and small amounts of methanol, water and other products. Based upon the methyl ester converted, the yield of resorcinol amounted to 39% and that of dihydroresorcinol to 25%

EXAMPLE II

A gas mixture comprising 4.0 moles of hydrogen and 2.2 moles of nitrogen per mole of methyl 5-oxo-hexanoate was passed for ten hours through the reactor described in Example I containing as catalyst, however, 8.8% by weight of copper and 3.3% by weight of nickel on silicon dioxide as a carrier; bulk density 0.5 g per ml. The catalyst was present in the form of little bars having a diameter of approximately 3 mm. and a length of about 5 mm. The temperature of the catalyst was about 345°–348°C. The catalyst had been activated by passing hydrogen through the reactor at 400°C for 24 hours. The space velocity mounted to 0.25 g of methyl ester per ml. of catalyst per hour. After an operating period of nine hours, the resulting gas mixture was passed for 1 hour through a collecting vessel which had been cooled to −20°C.

The weight of the condensed product, which had been heated to room temperature, amounted to 7.4 g. Gas-chromatographic analysis showed that the product contained 66.1% by weight of methyl 5-oxo-hexanoate, 7.8% by weight of resorcinol and 5% by weight of phenol. Based upon the converted quantity of methyl ester, the yield of resorcinol amounted to 30% and that of phenol to 25%.

EXAMPLE III

A gas comprising 9.0 moles of hydrogen and 4.5 moles of nitrogen per mole of ethyl 5-oxo-hexanoate was passed for eight hours through a reactor of the same type as that of Example I, containing as catalyst, however, 1.6% by weight of palladium and of 0.5% by weight of platinum on carbon in the form of little bars 2.4 mm in diameter and of 5 mm in length (bulk density 0.39 g per ml). The temperature of the catalyst was 344°–346°C. The catalyst had been activated by passing hydrogen through the reactor for 24 hours at a catalyst temperature of 300°C. The space velocity amounted to 0.15 g of the ethyl ester per ml of catalyst per hour.

After an operating period of 6 hours, the resulting gas mixture was passed for two hours through a collecting vessel which had been cooled to −20°C. The weight of the condensed product, which had been heated to room temperature, amounted to 6.0 g. Gas-chromatographic analysis showed that the product contained 73.2% by weight of ethyl 5-oxo-hexanoate and 14.5% by weight of resorcinol. Based upon the converted quantity of ethyl ester, the yield of resorcinol amounted to 77%.

EXAMPLE IV

In a similar way as in Example I, a gaseous mixture of hydrogen, nitrogen and methyl 5-oxo-hexanoate (9.0 moles of hydrogen and 4.5 moles of nitrogen per mole of the methyl ester) was passed through the tubular reactor for 30 hours.

In the reactor there were 20 ml of the palladium-platinum catalyst described in Example III, the temperature of the catalyst being about 322°–326°C. The space velocity amounted to 0.15 g of ester per ml. of catalyst per hour. After an operating period of 4 hours, the resulting gas mixture was led for 24 hours through a collecting vessel which had been cooled to −20°C. The weight of the condensed product, which had been heated to room temperature, amounted to 71.2 g.

Next, the gas mixture was made to condense for two hours in a second collecting vessel in a similar way. The product now obtained had a weight of 6.0 g and, according to gas-chromatographic analysis, contained 60.5% by weight of methyl 5-oxo-hexanoate, 25.3% by weight of resorcinol and 1.1% by weight of dihydroresorcinol. Based upon the converted quantity of methyl ester, the yield of resorcinol amounted to 84% and that of dihydroresorcinol to 4%.

The reaction product obtained first (71.2 g) was subjected to fractional distillation. The following fractions were obtained:

a. 5.9 g of product having a boiling range of 63°–66°C at atmospheric pressure,
b. 41.9 g of product having a boiling range of 91°–97°C at 11 mm. hg,
c. 15.1 g of product having a boiling range of 132°–140°C at 5 mm. hg.

Fraction (*a*) consisted of methanol, and fraction (*b*) methyl 5-oxo-hexanoate.

Fraction (*c*) crystallized during cooling. This fraction was dissolved in 200 g of boiling toluene, whereupon the resulting solution was cooled to room temperature. 13.5 G of resorcinol crystallized out and had a melting range of 110.0°–110.5°C.

EXAMPLE V

In the same way as in Example I, a gaseous mixture of hydrogen, nitrogen and methyl 5-oxo-4-methyl hexanoate (9.0 moles of hydrogen and 4.5 moles of nitrogen per mole of methyl 5-oxo-4-methylhexanoate) was led for sixteen hours through the reactor which contained 20 ml. of catalyst. The catalyst was the same as that used in Example III. The temperature of the catalyst was about 344°–346°C. The space velocity amounted to 0.16 g per ml. of catalyst per hour. After an operating period of 14 hours, the gas mixture obtained was made to condense for two hours and was analyzed as described in Example I.

The condensed product had a weight of 6.3 g and contained 22.0% by weight of 4-methylresorcinol, 53.2% by weight of the starting product and 13.9% by weight of 4-methylcyclohexane-1,3-dione. Based upon the converted quantity of the methyl ester, the yield of 4-methylresorcinol amounted to 59% and that of 4-methylcyclohexane-1,3-dione to 36%.

What is claimed is:

1. A process for the preparation of a resorcinol of the general formula:

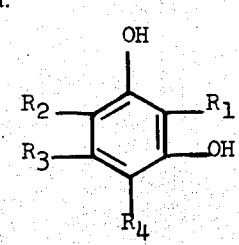

wherein $R_1$, $R_2$, $R_3$ and $R_4$, which are the same or different, are each hydrogen or an alkyl group containing up to 6 carbon atoms, and the total number of carbon atoms of $R_1$, $R_2$, $R_3$ and $R_4$ is no more than 12 carbon atoms, which comprises contacting a keto ester of the general formula

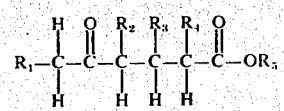

wherein $R_1$, $R_2$, $R_3$, and $R_4$ are as defined above and $R_5$ is an alkyl, cycloalkyl, or monocyclic or bicyclic aryl or arylalkyl group containing up to 12 carbon atoms, with a dehydrogenation catalyst wherein the dehydrogenation catalyst contains a metal or a compound of a metal selected from the group consisting of iron, cobalt, nickel, ruthenium rhodium, palladium, osmium, iridium, platinum and copper at a temperature of about 100°C to 500°C.

2. The process of claim 1 wherein the temperature is about 200° to 400°C and the reaction is carried out in the gaseous state.

3. The process of claim 1, wherein the keto ester is contacted with the catalyst in the gaseous state in the presence of hydrogen.

4. The process of claim 3 wherein the temperature is about 200° to 400°C and the reaction is carried out in the gaseous state.

5. The process of claim 4 wherein $R_5$ is an alkyl group of up to 6 carbon atoms.

6. A process for the preparation of a resorcinol of the general formula:

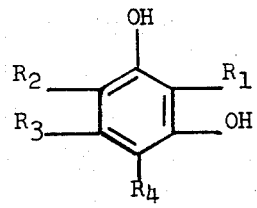

wherein $R_1$, $R_2$, $R_3$, and $R_4$, which are the same or different, are each hydrogen or an alkyl group containing up to 6 carbon atoms, and the total number of carbon atoms of $R_1$, $R_2$, $R_3$ and $R_4$ is no more than 12 carbon atoms, which comprises contacting a keto ester of the general formula

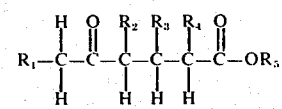

wherein $R_1$, $R_2$, $R_3$, and $R_4$ are as defined above and $R_5$ is an alkyl, cycloalkyl, or monocyclic or bicyclic aryl or arylalkyl group containing up to 12 carbon atoms, which keto ester is in the gaseous state, with a dehydrogenation catalyst comprising palladium, platinum, a mixture of palladium and platinum or nickel on a carrier at a temperature of 200°C to 400°C.

7. The process of claim 6 wherein the catalyst is palladium or platinum on a carbon carrier.

8. The process of claim 6 wherein the keto ester is contacted with the catalyst in the gaseous state in the presence of hydrogen.

9. The process of claim 6 wherein $R_5$ is an alkyl group of up to 6 carbon atoms.

10. The process of claim 7 wherein the keto ester is an alkyl 5-oxo-hexanoate containing up to 6 carbon atoms in the alkyl group.

11. The process of claim 6 wherein the keto ester is an alkyl 5-oxo-4-methylhexanoate containing up to 6 carbon atoms in the alkyl group.

* * * * *

UNITED STATES PATENT OFFICE
CERTIFICATE OF CORRECTION

Patent No. 3,950,438　　　　　　　　Dated April 13, 1976

Inventor(s) Sijbrandus E. Schaafsma et al

It is certified that error appears in the above-identified patent and that said Letters Patent are hereby corrected as shown below:

In the Heading Identification of FOREIGN APPLICATION PRIORITY DATA, change "Italy ..... 03537/70" to --Netherlands ..... 7303537--.

Signed and Sealed this

Thirteenth Day of July 1976

[SEAL]

*Attest:*

RUTH C. MASON  
*Attesting Officer*

C. MARSHALL DANN  
*Commissioner of Patents and Trademarks*